US008147801B2

(12) United States Patent
Demarest et al.

(10) Patent No.: US 8,147,801 B2
(45) Date of Patent: Apr. 3, 2012

(54) METHODS OF USING ALPHA-METHYLGLUCOSIDE (AMG) AS AN INDICATOR FOR GLUCOSE ABSORPTION AND EXCRETION

(75) Inventors: Keith T. Demarest, Flemington, NJ (US); James M. Lenhard, Fort Washington, PA (US); Gregory C. Leo, Lansdale, PA (US); Yin Liang, Owings Mills, MD (US); Tonya L. Martin, Quakertown, PA (US)

(73) Assignee: Janssen Pharmaceutica, N.V., Beerse (BE)

( * ) Notice: Subject to any disclaimer, the term of this patent is extended or adjusted under 35 U.S.C. 154(b) by 0 days.

(21) Appl. No.: 12/881,695

(22) Filed: Sep. 14, 2010

(65) Prior Publication Data

US 2011/0065200 A1     Mar. 17, 2011

Related U.S. Application Data

(60) Provisional application No. 61/242,570, filed on Sep. 15, 2009.

(51) Int. Cl.
    A61K 49/00         (2006.01)
(52) U.S. Cl. .......................................... 424/9.2; 424/9.1
(58) Field of Classification Search ........................ None
    See application file for complete search history.

(56) References Cited

U.S. PATENT DOCUMENTS

| 2005/0233988 A1 | 10/2005 | Nomura et al. |
| 2008/0027122 A1 | 1/2008 | Nomura et al. |
| 2008/0234367 A1 | 9/2008 | Washburn et al. |
| 2009/0099104 A1 | 4/2009 | Patel et al. |

FOREIGN PATENT DOCUMENTS

| EP | 1544208 A1 | 6/2005 |
| EP | 1557178 A1 | 7/2005 |
| WO | WO-2004081181 A2 | 9/2004 |

OTHER PUBLICATIONS

Moriya R, et al. Am. J. Physiol. Endocrinol. Metab. 297:E1358-1365, 2009.*
Bormans et al.; "Synthesis and Biologic Evaluation of $^{11}$C-Methyl-$_D$-Glucoside, a Tracer of the Sodium-Dependent Glucose Transporters," *Journal of Nuclear Medicine*, 2003; 44:1075-1081.
Boyd et al.; "Movements of Monosaccharides Between Blood and Tissues of Vascularly Perfused Small Intestine," *J Physiol.*, 1979; 287:371-391.
Calado et al.; "Novel compound heterozygous mutations in SLC5A2 are responsible for autosomal recessive renal glucosuria," *Human Genetics*, 2004; 114:314-316.
Debnam et al.; "An Experimental Method of Identifying and Quantifying the Active Transfer Electrogenic Component from the Diffusive Component During Sugar Absorption Measured in Vivo," *J Physiol.*, 1975; 246:181-196.
Ehrenkranz et al.; "Phlorizin: a review," *Diabetes Metab Res Rev*, 2005; 21:31-38.
Elsenhans et al.; "In-Vivo Inhibition by Polycations of Small Intestinal Absorption of Methyl $\alpha$-$_D$-Glucoside and Leucine in the Rat," *Biochem Pharmacol.*, 1989; 38(20):3423-3429.

Gatley, S. John; "Labeled Glucose Analogs in the Genomic Era," *J Nucl Med*, 2003; 44(7):1082-1086.
González Bosc et al.; Effect of Atrial Natriuretic Peptide on $\alpha$-Methyl-$_D$-Glucoside Intestinal Active Uptake in Rats, *Peptides*, 1998; 19(7):1249-1253.
Holzheimer et al.; "Influence of dietary fiber and intraluminal pressure on absorption and pre-epithelial diffusion resistance (unstirred layer) in rat jejunum in situ," *Naunyn Schmiedebergs' Arch Pharmacol*, 1986; 334:514-524.
Holzheimer et al.; "Influence of distension on absorption and villous structure in rat jejunum," *Am J Physiol Gastrointest Liver Physiol*, 1989; 256:G188-G197.
International Search Report from PCT/US2010/048752 dated Nov. 4, 2010, 6 pages.
Juan et al.; "Ontogenetic and regional changes in $\alpha$-methyl-$_D$-glucoside and $_L$-proline intestinal transport in guinea pig," *Am J Physiol*, 1998; 275:R897-R904.
Kanai et al.; "The Human Kidney Low Affinity NA $^+$/glucose Cotransporter SGLT2: Delineation of the Major Renal Reabsorptive Mechanism for $_D$-Glucose"; *J. Clin. Invest.*, 1994; 93:397-404.
Katsuno et al.; "Sergliflozin, a Novel Selective Inhibitor of Low-Affinity Sodium Glucose Cotransporter (SGLT2), Validates the Critical Role of SGLT2 in Renal Glucose Reabsorption and Modulates Plasma Glucose Level," *J Pharmacol Exp Ther*, 2007; 320(1):323-330.
Kimmich et al.; "$\alpha$-Methylglucoside satisfies only Na$^+$-dependent transport system of intestinal epithelium," *Am J Physiol*, 1981; 241:C227-C232.
Martin et al.; "Defects in Na$^+$/glucose cotransporter (SGLT1) trafficking and function cause glucose-galactose malabsorption," *Nat Genet*, 1996; 12:216-220.
Pajor et al.; "Cloning and Functional Expression of a Mammalian Na$^+$/Nucleoside Cotransporter"; *The Journal of Biological Chemistry*, 1992; 267(6):3557-3560.
Turk et al.; "Glucose/galactose malabsorption caused by a defect in the Na$^+$/glucose cotransporter," *Nature*, 1991; 350:354-356.
Ueta et al.; "Long-term treatment with the Na$^+$-glucose cotransporter inhibitor T-1095 causes sustained improvement in hyperglycemia and prevents diabetic neuropathy in Goto-Kakizaki Rats," *Life Sciences*, 2005; 76:2655-2668.
Van Den Heuvel et al.; "Autosomal recessive renal glucosuria attributable to a mutation in the sodium glucose cotransporter (SGLT2)," *Human Genetics*, 2002; 111:544-547.
Winne et al.; "Closed rat jejunal segment in situ: role or pre-epithelial diffusion resistance (unstirred layer) in the absorption process and model analysis," *Naunyn-Schmiedeberg's Arch Pharmacol*, 1987; 335:204-215.
Wright, Ernest M.; "Renal Na$^+$-glucose cotransporters," *Am J Physiol Renal Physiol*, 2001; 280:F10-F18.
You et al.; "Molecular Characteristics of Na$^+$-coupled Glucose Transporters in Adult and Embryonic Rat Kidney," *The Journal of Biological Chemistry*, 1995; 270(49):29365-29371.

* cited by examiner

*Primary Examiner* — Robert Landsman
(74) *Attorney, Agent, or Firm* — Venable LLP

(57) ABSTRACT

Presented here are methods using alpha-methylglucoside (AMG) in vivo as an indicator for glucose absorption from the gastrointestinal (GI) system or glucose excretion in the urine after oral administration of AMG. The methods find use in, for example, but not limited to, determining the effect of a sodium-dependent glucose transporter (SGLT) inhibitor in an animal, comparing the differences in the effects of a first and second SGLT inhibitor in an animal, and diagnosing a disease associated with glucose absorption from the gastrointestinal (GI) system or glucose excretion from the kidney in an animal.

11 Claims, 1 Drawing Sheet

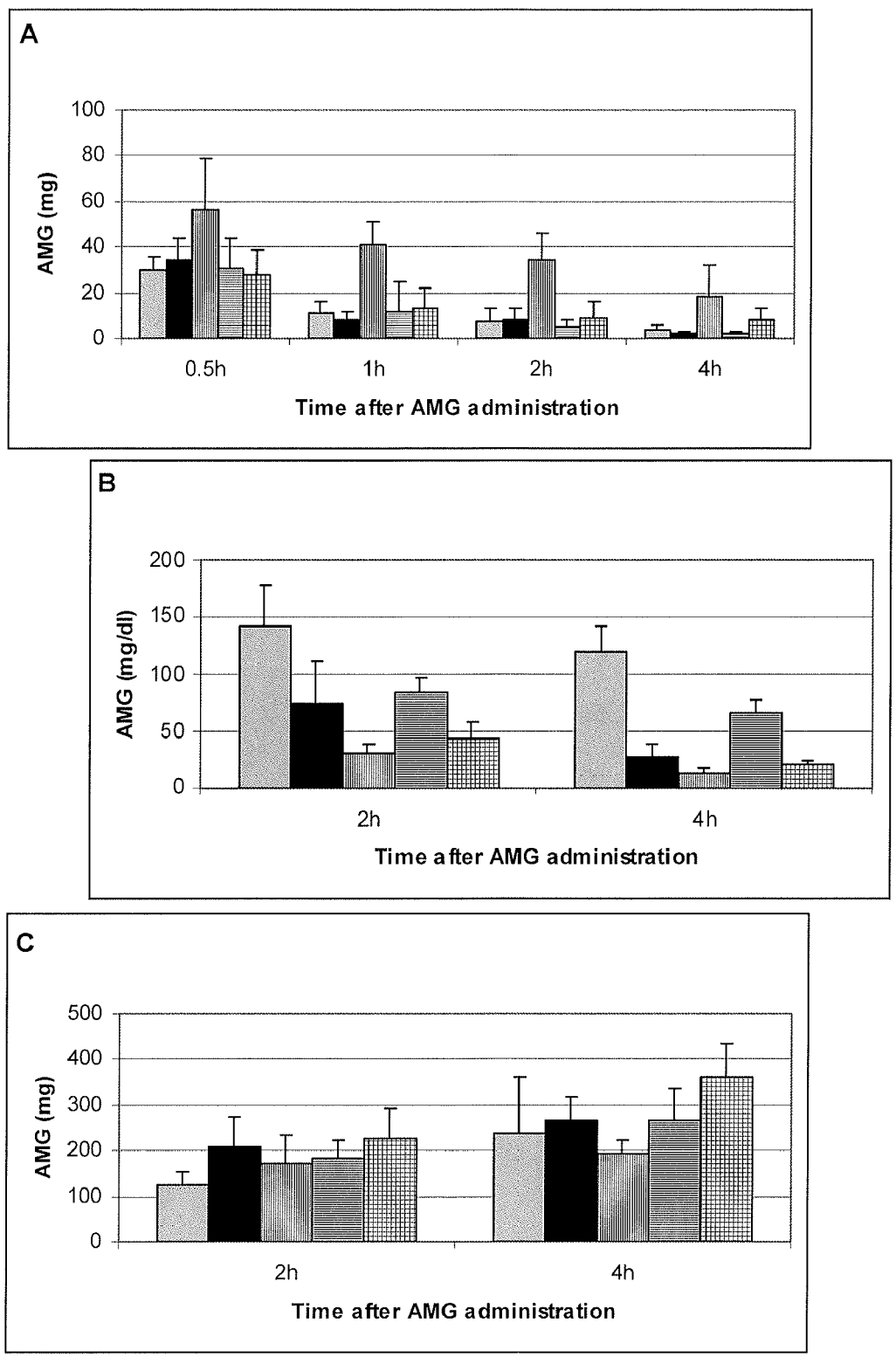

METHODS OF USING ALPHA-METHYLGLUCOSIDE (AMG) AS AN INDICATOR FOR GLUCOSE ABSORPTION AND EXCRETION

CROSS REFERENCE TO RELATED APPLICATIONS

This application claims benefit to U.S. Provisional Patent Application No. 61/242,570, filed Sep. 15, 2009, the contents of which are incorporated by reference herein in their entirety.

BACKGROUND OF THE INVENTION

I. Field of Invention

This invention relates to a method of using alpha-methylglucoside (AMG) in vivo as an indicator for glucose absorption from the gastrointestinal (GI) system, glucose re-absorption from the kidney tubules, and/or glucose excretion in the urine, after oral administration of AMG.

II. Description of Related Art

Hyperglycemia, that is, elevated plasma glucose, is a hallmark of diabetes. Type I diabetes mellitus, which comprises approximately 10% of diabetes cases, was previously referred to as insulin-dependent diabetes mellitus ("IDDM") or juvenile-onset diabetes. This disease is characterized by a progressive loss of insulin secretory function by beta cells of the pancreas. This characteristic is also shared by non-idiopathic, or "secondary", diabetes having its origins in pancreatic disease. Type I diabetes mellitus is associated with the following clinical signs or symptoms: persistently elevated plasma glucose concentration or hyperglycemia; polyuria; polydipsia and/or hyperphagia; chronic microvascular complications such as retinopathy, nephropathy and neuropathy; and macrovascular complications such as hyperlipidemia and hypertension which can lead to blindness, end-stage renal disease, limb amputation and myocardial infarction.

Type II diabetes mellitus (non-insulin-dependent diabetes mellitus or NIDDM) is a metabolic disorder involving the dysregulation of glucose metabolism and impaired insulin sensitivity. Type II diabetes mellitus usually develops in adulthood and is associated with the body's inability to utilize or make sufficient insulin. In addition to the insulin resistance observed in the target tissues, patients suffering from type II diabetes mellitus have a relative insulin deficiency, with lower than predicted insulin levels for a given plasma glucose concentration. Type II diabetes mellitus is characterized by the following clinical signs or symptoms: persistently elevated plasma glucose concentration or hyperglycemia; polyuria; polydipsia and/or hyperphagia; chronic microvascular complications such as retinopathy, nephropathy and neuropathy; and macrovascular complications such as hyperlipidemia and hypertension which can lead to blindness, end-stage renal disease, limb amputation and myocardial infarction.

Syndrome X, also termed Insulin Resistance Syndrome (IRS), Metabolic Syndrome, or Metabolic Syndrome X, is recognized in some 2% of diagnostic coronary catheterizations. Often disabling, it presents symptoms or risk factors for the development of Type II diabetes mellitus and cardiovascular disease, including impaired glucose tolerance (IGT), impaired fasting glucose (IFG), hyperglycemia, hyperinsulinemia, insulin resistance, dyslipidemia (e.g., high triglycerides, low HDL), hypertension and obesity.

Therapy for IDDM patients has consistently focused on administration of exogenous insulin, which may be derived from various sources (e.g., human, bovine, porcine insulin). The use of heterologous species material gives rise to formation of anti-insulin antibodies which have activity-limiting effects and result in progressive requirements for larger doses in order to achieve desired hypoglycemic effects.

Typical treatment of Type II diabetes mellitus focuses on maintaining the blood glucose level as near to normal as possible with lifestyle modification relating to diet and exercise, and when necessary, the treatment with anti-diabetic agents, or insulin, or a combination thereof. First-line therapy for NIDDM that cannot be controlled by dietary management is treatment with oral antidiabetic agents.

First-line therapies for NIDDM typically include metformin and sulfonylureas as well as thiazolidinediones. Metformin monotherapy is a first line choice, particularly for treating type II diabetic patients who are also obese and/or dyslipidemic. Lack of an appropriate response to metformin is often followed by treatment with metformin in combination with sulfonylureas, thiazolidinediones, or insulin. Sulfonylurea monotherapy (including all generations of drugs) is also a common first line treatment option. Another first line therapy choice may be thiazolidinediones. Alpha glucosidase inhibitors are also used as first and second line therapies. Patients who do not respond appropriately to oral anti-diabetic monotherapy are given combinations of the above-mentioned agents. When glycemic control cannot be maintained with oral antidiabetics alone, insulin therapy is used either as a monotherapy or in combination with oral antidiabetic agents.

Although insulin resistance is not always treated in all Syndrome X patients, those who exhibit a prediabetic state (e.g., IGT, IFG), where fasting glucose levels may be higher than normal but not at the diabetes diagnostic criterion, are treated in some countries (e.g., Germany) with metformin in an effort to prevent diabetes. The anti-diabetic agents may also be combined with other pharmacological agents for the treatment of the concomitant co-morbidities (e.g., antihypertensives for hypertension, hypolipidemic agents for lipidemia).

A recent development in treating hyperglycemia is focused on excretion of excessive glucose directly into the urine. Plasma glucose is normally filtered in the kidney in the glomerulus and actively reabsorbed in the proximal tubules. In particular, ninety percent of glucose reuptake in the kidney occurs in the epithelial cells of the early S1 segment of the renal cortical proximal tubule. Sodium-dependent glucose transporter 2 (SGLT2) appears to be the major transporter responsible for the reuptake of glucose at this site (Kanai et al., (1994) *J Clin Investig* 93: 397-404).

SGLT2 is a 672 amino acid protein containing 14 membrane-spanning segments that is predominantly expressed in the early S1 segment of the renal proximal tubules. The substrate specificity, sodium-dependence, and localization of SGLT2 are consistent with the properties of the high capacity, low affinity, sodium-dependent glucose transporter previously characterized in human cortical kidney proximal tubules. In addition, hybrid depletion studies in rats implicated SGLT2 as the predominant $Na^+$/glucose cotransporter in the S1 segment of the proximal tubule, since virtually all sodium-dependent glucose transport activity was inhibited by an antisense oligonucleotide specific to rat SGLT2 (You et al., (1995) *J Biol Chem.* 270(49):29365-71).

SGLT2 is also a candidate gene for some forms of familial glucosuria, a genetic abnormality in which renal glucose reabsorption is impaired to varying degrees (van den Heuvel et al., (2002) *Hum Genet* 111: 544-547; and Calado et al., (2004) *Hum Genet* 114: 314-316). The familial glycosuria syndromes are conditions in which intestinal glucose transport is normal and renal transport of other ions and amino acids is also normal. Familial glycosuria patients appear to develop normally, have normal plasma glucose levels, and appear to suffer no major health deficits as a consequence of their disorder, despite sometimes quite high (110-114 g/daily) levels of glucose excreted. The major symptoms evident in these patients include polyphagia, polyuria, and polydipsia. The kidneys appear to be normal in structure and function. Thus, from the evidence available so far, defects in renal reuptake of glucose appear to have minimal long term negative consequences in otherwise normal individuals. Studies of highly homologous rodent SGLTs also strongly implicate SGLT2 as the major renal sodium-dependent transporter of glucose and suggest that SGLT2 activity plays some role in glucosuria.

SGLT1, another sodium-dependent glucose cotransporter that is 60% identical to SGLT2 at the amino acid level, is expressed in the small intestine and in the more distal S3 segment of the renal proximal tubule (Pajor and Wright (1992) *J Biol Chem* 267: 3557-3560; and Wright (2001) *Am J Physiol* 280: F10-F18). Despite their sequence similarities, human SGLT1 and SGLT2 are biochemically distinguishable. For SGLT1, the molar ratio of Na$^+$ to glucose transported is 2:1. For SGLT2, the ratio is 1:1. The $K_m$ for Na$^+$ is 32 mM for SGLT1 and 250-300 mM for SGLT2. SGLT1 and SGLT2 also vary in their substrate specificities for some sugars, but the $K_m$ values for the uptake of glucose and the nonmetabolizable glucose analog, alpha-methylglucoside (AMG), are similar. For glucose, the $K_m$ values are 0.8 mM and 1.6 mM for SGLT1 and SGLT2, respectively. For AMG, $K_m$ values are 0.4 mM and 1.6 mM for SGLT1 and SGLT2, respectively (Kanai et al., (1994) *J Clin Investig* 93: 397-404; and U.S. Patent Application No. 2008/0234367).

Administration of phlorizin, a nonspecific SGLT1/SGLT2 inhibitor, provided in vivo proof of concept data for use of SGLT inhibitors to treat disorders associated with hyperglycemia (e.g., NIDDM and Syndrome X). Administration of phlorizin promoted glucose excretion, lowered fasting and fed plasma glucose levels, and promoted glucose utilization without hypoglycemic side effects in rodent models of diabetes and in one canine diabetes model (Ehrenkranz et al., (2005) *Diabetes Metab Res Rev* 21: 31-38). No adverse effects on plasma ion balance, renal function or renal morphology were observed as a consequence of phlorizin treatment for as long as two weeks. In addition, no hypoglycemic or other adverse effects were observed when phlorizin was administered to normal animals, despite the presence of glycosuria. Furthermore, long-term treatment with synthetic agents derived from phlorizin were reported to improve fasting and fed plasma glucose, improve insulin secretion and utilization in obese type II diabetes (NIDDM) rat models, and offset the development of nephropathy in the absence of hypoglycemic or renal side effects (Ueta et al., (2005) *Life Sci.* 76(23):2655-68).

Phlorizin itself, however, is unattractive as an oral drug because it is a nonspecific SGLT1/SGLT2 inhibitor and because it is hydrolyzed in the gut to the aglycone, phloretin. The hydrolyzed product is a potent inhibitor of facilitated glucose transporters (GLUTs) and concurrent inhibition of GLUTs is undesirable (Katsuno et al., (2007) *J Pharmacol Exp Ther.* 320(1):323-30). Such inhibitors would be predicted to exacerbate peripheral insulin resistance as well as promote hypoglycemia in the CNS. Inhibition of SGLT1 could also have serious adverse consequences as is illustrated by the hereditary syndrome glucose/galactose malabsorption (GGM), in which mutations in the SGLT1 cotransporter result in impaired glucose uptake in the intestine and life-threatening diarrhea and dehydration (Turk et al., (1991) *Nature* 350: 354-356; and Martin et al., (1996) *Nat Genet* 12: 216-220).

Taken as a whole, these data suggest that specific inhibition of SGLT2 in diabetic patients may safely normalize plasma glucose by enhancing the excretion of glucose in the urine, thereby improving insulin sensitivity and delaying the development of diabetic complications. Fortunately, the biochemical differences between SGLT2 and SGLT1, as well as the degree of sequence divergence between them, allow for identification of selective SGLT2 inhibitors. What are still needed, however, to further enable the discovery and optimization of such inhibitors, are assays to test the inhibitors in vivo and evaluate the effects of inhibitors with varying potency and selectivity for SGLT2 and SGLT1.

Glucose analogs have long been used for the study of glucose transport and for the characterization of glucose transporters (for review, see Gatley (2003) *J Nucl Med.* 44(7): 1082-6). Alpha-methylglucoside (AMG) is often the analog of choice for cell-based assays designed to study the activity of SGLT1 and/or SGLT2.

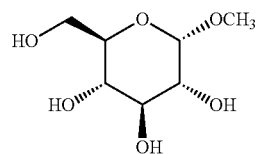

Alpha Methylglucoside (AMG)

Some Synonyms for Alpha Methylglucoside (AMG)

Alpha-D-Methylglucoside
Alpha-Methyl-D-glucoside
Methyl-Alpha-D-glucoside
Methyl α-D-Glucoside
1-O-Methyl-glucoside
Alpha-Methylglucopyranoside
Alpha-D-Methylglucopyranoside
Alpha-Methyl-D-glucopyranoside
Methyl-alpha-D-glucopyranoside
Methyl-α-D-glucopyranoside
1-O-Methyl-alpha-D-glucopyranoside
1-Methyl-alpha-D-glucopyranoside
Alpha-Methyl D-glucose ether AMG is a nonmetabolizable glucose analog. It is a substrate for both SGLT1 and SGLT2, with $K_m$ values similar to glucose for both transporters, which makes it an ideal indicator for studying the transport of glucose by SGLT1 and SGLT2. $K_m$ values for glucose are 0.8 mM and 1.6 mM for SGLT1 and SGLT2, respectively. $K_m$ values for AMG are 0.4 mM and 1.6 mM, respectively, for SGLT1 and SGLT2 (Kanai et al., (1994) *J Clin Investig* 93: 397-404; and U.S. Patent Application No. 2008/0234367). Furthermore, it has been demonstrated that $^{11}$C-labelled-AMG, administered by injection via a tail vein, can be used as a selective tracer of glucose transport and can be used to visualize the function of different transporters with PET imaging done in vivo (Bormans et al., (2003) *Journal of Nuclear Medicine*, 44(7):1075-1081).

A potential problem using AMG for in vivo studies of glucose transport is that it has been demonstrated that AMG is not a substrate for the intestinal serosal transport system. For example, it has been shown that AMG accumulates in isolated chicken intestinal epithelial cells. It was determined that as a result of unidirectional flux into the epithelial cells, steady-state gradients of AMG are accurately represented by a concentrative process that is only opposed by a diffusional efflux process. (Kimmich and Randles (1981) *Am J Physiol.* 241(5): C227-32). In addition, studies using vascularly perfused preparations of the small intestine of the frog, *R. ridibunda*, showed that AMG loaded into the epithelium from the lumen washed out of the cells only slowly into the vascular bed, so that even with high rates of vascular perfusion AMG accumulated within the tissue (Boyd and Parsons (1979) J Physiol. 287:371-91). Absorption of AMG has also been demonstrated ex vivo, in small intestine and colon tissue sleeve preparations from male Wistar rats (González Bosc et al., (1998) *Peptides.* 19(7):1249-53), and in everted sleeves of duodenum, jejunum, and ileum, from male Dunkin Hartley guinea pigs (*Cavia porcellus*) (Juan et al., (1998) *Am J Physiol.* 275(3 Pt 2):R897-904). The nature of the ex vivo experiments, however, precluded the subsequent measurement of AMG in blood, urine, or other tissues. Furthermore, experiments showing that AMG accumulates in cells and tissues suggested that AMG would not pass through in appreciable amounts to blood or urine because AMG is not a substrate for the intestinal serosal transport system.

Using male rats cannulated in a section of the mid-jejunum, absorption of $^{14}$C-AMG was calculated as "luminal loss", i.e., the amount initially circulated in a segment of the jejunum minus that recovered after circulating a solution for 15 minutes. For these experiments, $^{14}$C-AMG was not subsequently measured in plasma, urine, or any tissues (Debnam Levin (1975) *J Physiol.* 246(1):181-96). Similarly, $^{14}$C-AMG uptake was measured with single-pass perfusion of cannulated segments of the jejunum from female Wistar rats. Again, subsequent measurements of AMG in blood or urine were not reported (Elsenhans and Schümann (1989) *Biochem Pharmacol.* 38(20):3423-9). In experiments done in situ, using a closed jejunal segments from male a Wistar rats, absorption of $^{14}$C-AMG was determined by the appearance rate in intestinal venous blood after injection into the closed jejunal segments (Winne et al., (1987) *Naunyn Schmiedebergs Arch Pharmacol.* 335(2):204-15). In another study, the influence of dietary fiber, intraluminal pressure, and distension on absorption were investigated with the same methods (Holzheimer and Winne (1986) *Naunyn Schmiedebergs Arch Pharmacol.* 334:514-524; and Holzheimer and Winne (1989) *Am J Physiol.* 256 (1 Pt 1):G188-97). Experiments done in situ using $^{14}$C-AMG injected into closed jejunal segments did not show that AMG could be used in vivo as an indicator for glucose absorption from the gastrointestinal (GI) system, glucose re-absorption from the kidney tubules, and/or glucose excretion in the urine, after oral administration of AMG.

SUMMARY OF THE INVENTION

The various features of novelty which characterizes the invention are pointed out with particularity in the claims annexed to and forming a part of the disclosure. For a better understanding of the invention, its operating advantages, and specific objects attained by its use, reference should be had to the drawing and descriptive matter in which there are illustrated and described embodiments of the invention.

In one embodiment, the present invention comprises a method for using alpha-methylglucoside (AMG) as an indicator for glucose absorption from the gastrointestinal system or glucose excretion from the kidney of an animal, comprising the steps of: (a.) administering an oral dose of a predetermined amount of AMG to said animal; (b.) obtaining a sample from said animal after AMG administration; (c.) measuring the amount of said AMG in said sample; wherein the amount of AMG in said sample correlates to the amount of glucose absorption from the gastrointestinal system of said animal or the amount of glucose excretion from the kidney of the animal.

In a second embodiment, the present invention comprises the method described above, wherein the animal is selected from the group consisting of: mice, rats, hamsters, guinea pigs, dogs, pigs, non-human primates, and humans.

In a third embodiment, the present invention comprises the method described above, wherein the sample is selected from the group consisting of: plasma, urine, and the gastrointestinal tract.

In a fourth embodiment, the present invention comprises a method for determining the effect of an SGLT inhibitor in an animal, comprising the steps of: (a.) administering a predetermined amount of the SGLT inhibitor to a first animal; (b.) administering an oral dose of a predetermined amount of alpha-methylglucoside (AMG) to said first animal, and to a second animal, said second animal is not administered with said SGLT inhibitor; (c.) obtaining a samples from said first and second animals; (d.) measuring the amounts of AMG in said samples; (e.) comparing the amount of AMG in the sample from said first animal to the amount of AMG in the sample from said second animal; wherein the difference in the amount of said AMG in said samples demonstrates the effect of said SGLT inhibitor in said first animal.

In a fifth embodiment, the present invention comprises the method described above, wherein the SGLT inhibitor is selected from the group consisting of: SGLT2 inhibitors and SGLT1 inhibitors.

In a sixth embodiment, the present invention comprises the method described above, wherein the animal is selected from the group consisting of: mice, rats, hamsters, guinea pigs, dogs, pigs, non-human primates, and humans.

In an seventh embodiment, the present invention comprises the method described above, wherein the sample is selected from the group consisting of: plasma, urine, and the gastrointestinal tract.

In an eighth embodiment, the present invention comprises a method for comparing the differences in the effects of a first and second SGLT inhibitor, where in the method comprises the steps of: (a.) administering a predetermined amount of said first SGLT inhibitor to a first animal; (b.) administering a predetermined amount of said second SGLT inhibitor to a second animal; (c.) administering an oral dose of a predetermined amount of alpha-methylglucoside (AMG) to said first and second animals; (d.) obtaining samples from said first and second animals; (e.) measuring the amounts of AMG in said samples; (f.) comparing the amount of AMG in the sample from said first animal to the amount of AMG in the sample from said second animal; wherein the difference in the amounts of AMG in said samples provides a basis for comparing the differences in the effects of said first and second SGLT inhibitors.

In a ninth embodiment, the present invention comprises the method described above, wherein the first and second SGLT inhibitors are selected from the group consisting of: SGLT2 inhibitors and SGLT1 inhibitors.

In a tenth embodiment, the present invention comprises the method described above, wherein the animal is selected from the group consisting of: mice, rats, hamsters, guinea pigs, dogs, pigs, non-human primates, and humans.

In a eleventh embodiment, the present invention comprises the method described above, wherein the sample is selected from the group consisting of: plasma, urine, and the gastrointestinal tract.

In a twelfth embodiment, the present invention comprises a method for diagnosing a disease associated with glucose absorption from the gastrointestinal (GI) system or glucose excretion from the kidney in an animal, comprising the steps of: (a.) administering respectively an oral dose of a predetermined amount of AMG to a first animal and to a second animal that is free from said disease; (b.) obtaining samples from said first and second animals; (c.) measuring the amounts of AMG in said samples; (d.) comparing the amount of said AMG in the sample from said first animal to the amount of AMG in the sample obtained from said second animal; wherein the difference in the amounts of AMG in said samples provides a basis to determine whether said first animal has the disease associated with glucose absorption from the gastrointestinal (GI) system or glucose excretion from the kidney.

In a thirteenth embodiment, the present invention comprises the method described above, wherein the animals are humans.

In a fourteenth embodiment, the present invention comprises the method described above, wherein the samples are selected from the group consisting of: plasma or urine.

BRIEF DESCRIPTION OF THE DRAWINGS

In the drawings:

FIGS. 1A-1C: Shown are the amounts of AMG, units in milligrams (mg) or milligrams per decilitre (mg/dl), measured after different treatments with Vehicle (0.5% methylcellulose (methocel)), and Compound 1 or Compound 2 suspended in 0.5% methylcellulose, in samples taken from GI tract (A), plasma (B), and urine (C). Gray shaded bars are for Vehicle-treated rats, black bars are for Compound 2-treated rats at 0.3 mpk; the vertically striped bars are for Compound 2-treated rats at 3.0 mpk; the horizontally striped bars are for Compound 1-treated rats at 0.3 mpk; and the hatched bars are for Compound 1-treated rats at 3.0 mpk.

DETAILED DESCRIPTION OF THE PRESENTLY PREFERRED EMBODIMENTS

To illustrate the invention, various exemplary embodiments are described below. It is to be understood at the outset, that the figures and examples provided herein are to exemplify, and not to limit the invention and its various embodiments. For the sake of brevity, the disclosures of all patents and other publications cited in this section are incorporated herein in their entirety by reference.

In one particular embodiment, the present invention comprises a method for using alpha-methylglucoside (AMG) as an indicator for glucose absorption from the gastrointestinal (GI) system of an animal, glucose re-absorption from the kidney tubules of an animal, and glucose excretion in the urine of an animal, after oral administration of AMG. The AMG, as an indicator, may be used in a number of ways depending on the intended purposes as described in the present invention. For example, AMG may be used to diagnose a disease associated with defects in absorption, metabolism, or excretion of glucose. AMG may also be used to screen drug candidates for the treatment of Type II diabetes mellitus (non-insulin-dependent diabetes mellitus or NIDDM) and Syndrome X, also termed Insulin Resistance Syndrome (IRS), Metabolic Syndrome, or Metabolic Syndrome X. Nonlimiting examples of drug candidates include pharmacolgical agents such as SGLT inhibitors with varying selectivity for SGLT2 and SGLT1. Mixtures of agents may also be employed.

Nonlimiting examples of animals that are contemplated for use in the present invention include mammals such as dogs, pigs, non-human primates, humans, and rodents such as a rats, mice, hamsters, and guinea pigs.

AMG of the present invention may be obtained from a commercial source or produced by synthetic methods commonly known to a person skilled in the art. Those skilled in the art will also recognize that AMG for use in the method of the present invention may be labeled or modified with any suitable agent to aid in detection and quantification. For example, AMG may be labelled with a chromogenic, fluorogenic, or radioactive agent. In one nonlimiting example of the present invention, because of the NMR method of detection that was used, AMG did not require any label to aid in detection and quantification of AMG in the sample.

Many different techniques can be used to detect and quantify orally administered AMG in samples of the present invention. The techniques include, but are not limited to, any chromatographic means that separates AMG from other components in a sample, such as high pressure liquid chromatography (HPLC) and mass spectrometry (MS), alone or in combination; any chromogenic detection means; any fluorometric detection means; any radioactive detection means; and any nuclear magnetic resonance (NMR) means. In one nonlimiting example of the present invention, orally administered AMG is detected in samples using an NMR spectrometer to detect the anomeric proton of unlabelled or modified AMG, which is a doublet at 4.80 ppm in the NMR spectrum. The amount of AMG present in the sample is quantified by comparison to an internal reference, DSS (2,2-dimethyl-2-silapentane-$d_6$-sulfonic acid, sodim salt) at 0.00 ppm. Currently available NMR instrumentation will allow for a detection limit of approximately 0.2 mg/dl AMG, which is approximately 10 uM AMG. MS analysis, however, is more sensitive, even though AMG does not ionize well. Using MS would make it possible to detect sub-uM amounts of AMG. Those skilled in the art will appreciate that further improvements in the limits of detection could also be made by using labeled AMG, although in such a case the advantages of using an unlabelled indicator would be compromised. NMR sample sizes depend on the type of instrumentation used, but in a nonlimiting example sample size could range from approximately 5 to 500 ul.

AMG of the present invention is preferably administered orally. Nonlimiting examples of oral administration include oral gavage, solid oral doses, or including AMG with food as part of the diet. The oral regimens of AMG may also include a carrier or other agent that improves the solubility or availability of AMG. In a nonlimiting example of the present invention, AMG was dissolved in sterile water and administered orally via gavage at a dose of about 2 g/kg (AMG/body weight). Those skilled in the art will appreciate that the dose may be increased or decreased, depending on the method of detection or whether or not labelled or unlabelled AMG is used.

As used herein, the term "sample(s)" includes blood and other bodily fluid that can be taken directly from an animal with minimally invasive or non-invasive approaches (e.g., urine collection, blood drawing, needle aspiration, and other procedures involving minimal risk, discomfort or effort). A sample may also encompass serum, plasma, other bodily fluids or tissues, such as tissue lysates, cell supernatants, cell lysates, or the like. Nonlimiting examples of the specific types of samples contemplated in the present invention include urine, plasma, fluid contents of the stomach, or a lysate prepared from surgically removed portions of the gastrointestinal system, kidney, or urinary tract. In a preferred embodiment, urine, plasma, and a lysate prepared from a sample taken from the gastrointestinal system, are prepared for the uses described in the present invention.

Samples may be manipulated in any way after their procurement, such as by treatment with reagents to solubilize, enrich, or deplete certain components, such as proteins or polynucleotides for the purpose of obtaining optimal testing results.

According to the present invention, the samples may be taken once or multiple times at regular intervals after oral administration of AMG. In one nonlimiting example, samples were taken at 120 or 240 minutes after oral administration of AMG to the animals. The animals were sacrificed, urine and plasma samples were collected, and the entire gastrointestinal (GI) tracts were removed and placed into saline. Subsequently, lysates were made of the GI tracts. Aliquots were taken from plasma, urine and the GI tract lysates and all samples were extracted with acetonitrile to precipitate protein. It is desirable to remove proteins because different samples may contain greatly differing amounts of proteins.

Also, according to the present invention, AMG administrated orally is not only absorbed from the gastrointestinal (GI) system, but also appears in appreciable levels in the plasma or urine. As described in the present invention, oral administration of AMG causes no complication resulting from metabolism of the AMG in the animals, therefore quantification of the AMG in various samples (for example, GI tract, plasma, and urine) is simplified. This allows for differentiation of compounds that affect glucose absorption from those that affect glucose excretion or those that affect both. Also, because of the NMR methods employed to detect and quantify unlabelled AMG, radioactive isotopes are no longer required. Absent the NMR methodology of the present invention, such radioactive isotopes would have been required as described in the study of $^{11}$C AMG distribution using PET imaging after intravenous injection of $^{11}$C labeled AMG (Bormans et al., (2003) *Journal of Nuclear Medicine*, 44(7): 1075-1081).

The present invention also demonstrates that SGLT inhibitors, with varying potency and selectivity for SGLT1 and SGLT2, cause quantifiably different amounts of AMG to be found in the GI tract, plasma, urine or other places in the body after AMG administration. Furthermore, the AMG amounts in the GI tract, plasma, or urine, etc., are shown to be dose dependent. Thus AMG administrated orally can be used as an indicator for glucose absorption from the GI system, glucose re-absorption from the kidney tubules, and glucose excretion in the urine.

Without further description, it is believed that one of ordinary skill in the art can, using the preceding description and the following illustrative examples, make and utilize the present invention and practice the claimed methods. The following working examples therefore, specifically point out preferred embodiments of the present invention, and are not to be construed as limiting in any way the remainder of the disclosure.

EXAMPLE 1

Cell-based Assays

Inhibition of SGLT activity with Compound 1 and Compound 2 was assessed in CHOK1 cells stably expressing either human SGLT1 or human SGLT2. Compound 1 and Compound 2, are described in U.S. Patent Application Nos. 2005/0233988 and 2008/0027122, the contents of which are incorporated by reference in their entirety.

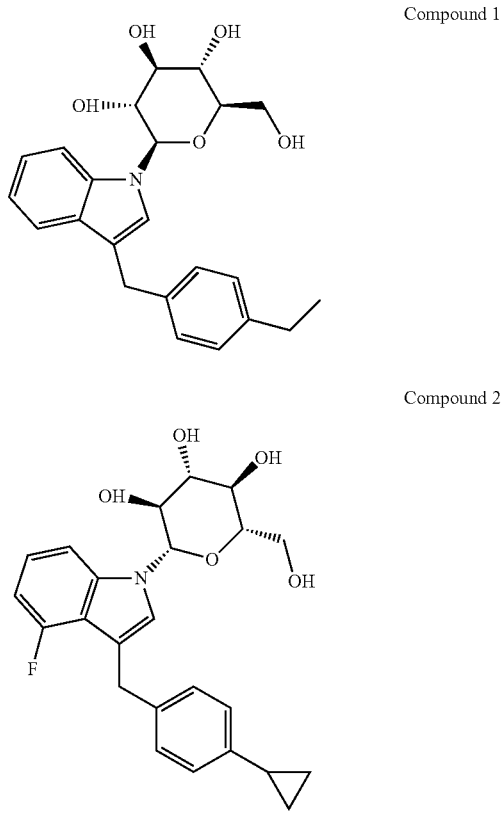

CHOK1 cells expressing human SGLT2 or human SGLT1 were seeded in 24-well plates at a density of approximately 400,000 cells/well in F-12 nutrient mixture (Ham's F-12) containing 10% fetal bovine serum, 400 ug/ml Geneticin, 50 units/ml sodium penicillin G (Gibco-BRL) and 50 ug/ml streptomycin sulfate. Cells were maintained in culture for 2 days at 37° C. in a humidified atmosphere containing 5% $CO_2$. On the day of the assay, Compound 1 and Compound 2 were dissolved in DMSO and then diluted in assay buffer. The final concentration of DMSO was 0.5%. Assay buffer contained 137 mM NaCl, 5 mM KCl, 1 mM $CaCl_2$, 1 mM $MgCl_2$, 50 mM Hepes, and 20 mM Tris, pH 7.4. To start the assay, cells were washed once with the assay buffer and then incubated with 250 ul of the assay buffer containing Compound 1 or Compound 2 for 10 min at 37° C. The transport reaction was initiated by addition of 50 ul $^{14}$C-AMG solution (final concentration, 0.5 mM $^{14}$C-AMG). After incubation for 30 minutes at 37° C., the uptake was stopped by aspiration of the incubation mixture and the cells were washed three times with ice-cold PBS. Cells were then solubilized with 0.3 N NaOH and aliquots were taken for determination of radioactivity by a liquid scintillation counter. Nonspecific AMG uptake was defined as that which occurred in the presence of 100 uM of phlorizin, a specific inhibitor of sodium-dependent glucose cotransporter. Specific uptake was normalized for the protein concentrations measured by the method of Bradford. The 50% inhibitory concentration ($IC_{50}$) values were calculated from dose-response curves by least square method. The $IC_{50}$ values for the cell-based SGLT2 and SGLT1 assay are presented in Table 1.

TABLE 1

IC$_{50}$ values (nM) for human SGLT1 and SGLT2.

| Compound | hSGLT1 (IC50, nM) [A] | hSGLT2 (IC50, nM) [B] | [A]/[B] (fold) |
|---|---|---|---|
| Compound 1 | 1700 | 8.4 | 202 |
| Compound 2 | 270 | 1.9 | 142 |

EXAMPLE 2

Animal Studies

Male Sprague-Dawley (SD) rats were dosed by oral gavage with either vehicle, 0.5% methylcellulose (methocel) in sterile water, or one of the SGLT inhibitors (Compound 1 and Compound 2) at 0.3 or 3.0 mg/kg. Compounds were administered as a suspension in 0.5% methylcellulose and sterile water. One hour after dosing the animals with the compounds, AMG was administrated orally via gavage (2 g/kg). AMG was dissolved in sterile water. Rats were sacrificed 120 or 240 minutes after AMG administration. Urine and plasma samples were collected and the entire gastrointestinal tract was removed and placed into saline. Subsequently, a GI lysate was made. Aliquots were taken from the samples of plasma, urine and the GI lysate and were extracted with acetonitrile to precipitate protein. It was desirable to remove the protein because the different biofluids contain greatly differing amounts of protein. The protein signal could have rendered more difficult the quantification of the AMG. The aqueous portion was dried down and re-suspended in deuterated water to a volume of 0.5 ml. The use of deuterated water made possible the observation of the anomeric proton in the NMR spectrum as the anomeric proton resonates in a much less crowded region of the spectrum. The methyl singlet possibly could have also been used but suffers from overlap with other metabolite signals.

EXAMPLE 3

In vivo Data Analysis

Proton NMR spectra were acquired on a Bruker DMX 600 MHz NMR spectrometer (Bruker Biospin Corporation, Billerica, Mass.) with the probe temperature maintained at 32° C. The mildly elevated temperature was used to enhance the chemical shift separation between the solvent peak (the residual water in the sample) and the anomeric proton of AMG (a doublet at 4.80 ppm) which was used for quantification. The solvent peak was saturated using very low power irradiation (a field strength of about 4 Hz) during the pre-pulse delay followed by a 30° pulse to acquire the signal. The pre-pulse delay was 3.0 s and the acquisition time was 2.1 s. The sweep width was 13 ppm using 32 k complex points. Before fourier transformation the data was apodized with 0.5 Hz exponential linebroadening. The amount of AMG present in the sample was determined relative to an internal reference, DSS (2,2-dimethyl-2-silapentane-d$_6$-sulfonic acid, sodim salt) at 0.00 ppm.

The in vivo results showed that in vehicle treated rats, AMG is absorbed from the GI system and can be detected in GI system, plasma, and urine samples, FIGS. 1A, 1B, and 1C, respectively. In rats treated with Compound 2 (SGLT1 IC$_{50}$=270 nM), the AMG content retained in the GI system was markedly increased at the higher dose (FIG. 1A). Treatment with Compound 1 (IC$_{50}$ on SGLT1=1700 nM) did not cause a significant retention of AMG in the GI system. Both Compound 1 and Compound 2 showed dose-dependent decreases in the amount of AMG detected in plasma (FIG. 1B). For Compound 1, the dose-dependent decrease in the amount of AMG detected in plasma is attributed to the potent inhibition of SGLT2 (SGLT2 IC$_{50}$=8.4 nM) and the resulting increase in the amount of AMG detected in the urine (FIG. 1C). For Compound 2, the dose-dependent decrease in the amount of AMG in the plasma is attributed to both the inhibitory effect on SGLT1 (SGLT1 IC$_{50}$=270 nM) in the GI system resulting in a decrease in GI absorption of AMG (FIG. 1A) and to the potent inhibition of SGLT2 (SGLT2 IC$_{50}$=1.9 nM) in the kidneys resulting in the increased amount of AMG detected in the urine (FIG. 1C).

Thus, while there have been shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

The invention claimed is:

1. A method for determining the effect of a sodium-dependent glucose transporter (SGLT) inhibitor in an animal, comprising the steps of:
   a. administering a predetermined amount of the SGLT inhibitor to a first animal;
   b. administering an oral dose of a predetermined amount of alpha-methylglucoside (AMG) to said first animal, and to a second animal, said second animal is not administered with said SGLT inhibitor;
   c. obtaining samples from said first and second animals;
   d. measuring the amounts of AMG in said samples; and
   e. comparing the amount of AMG in the sample from said first animal to the amount of AMG in the sample from said second animal;
   wherein the difference in the amount of said AMG in said samples demonstrates the effect of said SGLT inhibitor in said first animal.

2. The method as in claim 1, wherein the SGLT inhibitor is selected from the group consisting of: SGLT2 inhibitors and SGLT1 inhibitors.

3. The method of claim 1, wherein the animal is selected from the group consisting of: mice, rats, hamsters, guinea pigs, dogs, pigs, non-human primates, and humans.

4. The method of claim 1, wherein the sample is selected from the group consisting of: plasma, urine, and gastrointestinal tract.

5. A method for comparing the differences in the effects of a first and second sodium-dependent glucose transporter (SGLT) inhibitor, comprising the steps of:
   a. administering a predetermined amount of said first SGLT inhibitor to a first animal;
   b. administering a predetermined amount of said second SGLT inhibitor to a second animal;

c. administering an oral dose of a predetermined amount of alpha-methylglucoside (AMG) to said first and second animals;
d. obtaining samples from said first and second animals;
e. measuring the amounts of AMG in said samples; and
f. comparing the amount of AMG in the sample from said first animal to the amount of AMG in the sample from said second animal;
wherein the difference in the amounts of AMG in said samples provides a basis for comparing the differences in the effects of said first and second SGLT inhibitors.

6. The method as in claim 5, wherein the first and second SGLT inhibitors are selected from the group consisting of: SGLT2 inhibitors and SGLT1 inhibitors.

7. The method of claim 5, wherein the animal is selected from the group consisting of: mice, rats, hamsters, guinea pigs, dogs, pigs, non-human primates, and humans.

8. The method of claim 5, wherein the sample is selected from the group consisting of: plasma, urine, and gastrointestinal tract.

9. A method for diagnosing a disease associated with glucose absorption from the gastrointestinal (GI) system or glucose excretion from the kidney in an animal, comprising the steps of:
a. administering respectively an oral dose of a predetermined amount of alpha-methylglucoside (AMG) to a first animal and to a second animal that is free from said disease;
b. obtaining samples from said first and second animals;
c. measuring the amounts of AMG in said samples; and
d. comparing the amount of said AMG in the sample from said first animal to the amount of AMG in the sample obtained from said second animal;
wherein the difference in the amounts of AMG in said samples provides a basis to determine whether said first animal has the disease associated with glucose absorption from the gastrointestinal (GI) system or glucose excretion from the kidney.

10. The method of claim 9, wherein the animal is a human.

11. The method of claim 9, wherein said sample is plasma or urine.

* * * * *